US011197776B2

(12) United States Patent
Anderson et al.

(10) Patent No.: US 11,197,776 B2
(45) Date of Patent: *Dec. 14, 2021

(54) METHOD AND APPARATUS FOR CRYOGENIC TREATMENT OF SKIN TISSUE

(71) Applicant: The General Hospital Corporation, Boston, MA (US)

(72) Inventors: Richard Rox Anderson, Boston, MA (US); Dieter Manstein, Coral Gables, FL (US); Henry Hin Lee Chan, Mid-level (HK); Joseph Ting, Framingham, MA (US)

(73) Assignee: The General Hospital Corporation, Boston, MA (US)

( * ) Notice: Subject to any disclaimer, the term of this patent is extended or adjusted under 35 U.S.C. 154(b) by 490 days.

This patent is subject to a terminal disclaimer.

(21) Appl. No.: 15/984,794

(22) Filed: May 21, 2018

(65) Prior Publication Data

US 2019/0029876 A1    Jan. 31, 2019

Related U.S. Application Data

(63) Continuation of application No. 14/358,359, filed as application No. PCT/US2012/065643 on Nov. 16, 2012, now Pat. No. 9,974,684.

(Continued)

(51) Int. Cl.
*A61B 18/02* (2006.01)
*A61F 7/00* (2006.01)
*A61B 18/00* (2006.01)

(52) U.S. Cl.
CPC ............ *A61F 7/0085* (2013.01); *A61B 18/02* (2013.01); *A61F 7/007* (2013.01);
(Continued)

(58) Field of Classification Search
CPC .......... A61B 18/02; A61B 2018/00452; A61B 2018/0047; A61B 2018/00791;
(Continued)

(56) References Cited

U.S. PATENT DOCUMENTS 3,664,344 A    5/1972   Bryne
4,206,609 A    6/1980   Durenec
(Continued)

FOREIGN PATENT DOCUMENTS

DE    9217897        11/1993
DE    9217897 U1     11/1993
(Continued)

OTHER PUBLICATIONS

Y. Har-shai et al. "Effect of Skin Temperature on Skin Pigmentation During Contact and Intralesional Cryosurgery of Keloids" JEADV 2007, 21, pp. 191-198.
(Continued)

*Primary Examiner* — Michael F Peffley
*Assistant Examiner* — Amanda L Zink
(74) *Attorney, Agent, or Firm* — Hunton Andrews Kurth LLP

(57) ABSTRACT

Cosmetic method and apparatus are provided that can provide cooling and/or freezing of skin tissue proximal to the skin surface to generate an appearance of lightening or reduced pigmentation in the skin. The skin can be cooled to a temperature of less than about −5 degrees Celsius for a duration of about one minute or less, using a plurality of cooled contact surfaces, each having a width between about 2 mm and about 20 mm. A cooling arrangement can be provided to provide controlled heat removal from the skin tissue being treated. A sensor can optionally be provided to detect freezing of tissue proximal to the cooled surfaces.

16 Claims, 7 Drawing Sheets

Related U.S. Application Data

(60) Provisional application No. 61/560,621, filed on Nov. 16, 2011.

(52) U.S. Cl.
CPC ............... *A61B 2018/0047* (2013.01); *A61B 2018/00452* (2013.01); *A61B 2018/00791* (2013.01); *A61B 2018/00875* (2013.01); *A61B 2018/0237* (2013.01); *A61B 2018/0262* (2013.01); *A61F 2007/0052* (2013.01); *A61F 2007/0056* (2013.01); *A61F 2007/0075* (2013.01); *A61F 2007/0094* (2013.01); *A61F 2007/0095* (2013.01)

(58) Field of Classification Search
CPC .. A61B 2018/00875; A61B 2018/0237; A61B 2018/0262; A61F 2007/0052; A61F 2007/0056; A61F 2007/0075; A61F 2007/0094; A61F 2007/0095; A61F 7/007; A61F 7/0085
See application file for complete search history.

(56) References Cited

U.S. PATENT DOCUMENTS

| | | | |
|---|---|---|---|
| 4,614,191 | A | 9/1986 | Perler |
| 5,596,875 | A | 1/1997 | Berry et al. |
| 5,759,182 | A | 6/1998 | Varney et al. |
| 5,848,981 | A | 12/1998 | Herbranson |
| 6,017,337 | A | 1/2000 | Pira |
| 6,430,956 | B1 | 8/2002 | Haas et al. |
| 6,503,246 | B1 | 1/2003 | Har-Shai et al. |
| 6,629,417 | B2 | 10/2003 | Haas et al. |
| 6,981,970 | B2 | 1/2006 | Karni |
| 7,630,774 | B2 | 12/2009 | Karni et al. |
| 7,751,452 | B2 | 7/2010 | Vogler |
| 7,850,683 | B2 | 12/2010 | Elkins |
| 8,150,532 | B2 | 4/2012 | Karni et al. |
| 8,435,194 | B2 | 5/2013 | Dverin et al. |
| 8,579,835 | B2 | 11/2013 | Britva et al. |
| 8,950,406 | B2 | 2/2015 | Karni |
| 2003/0100936 | A1 | 5/2003 | Altshuler et al. |
| 2005/0015121 | A1 | 1/2005 | Molina |
| 2005/0222565 | A1 | 10/2005 | Manstein et al. |
| 2006/0189976 | A1 | 8/2006 | Karni et al. |
| 2007/0088386 | A1 | 4/2007 | Eilaz |
| 2007/0129714 | A1 | 6/2007 | Elkins |
| 2007/0135876 | A1 | 6/2007 | Weber |
| 2007/0185527 | A1 | 8/2007 | Eilaz |
| 2008/0039747 | A1 | 2/2008 | Baerwalde et al. |
| 2008/0077211 | A1 | 3/2008 | Levinson |
| 2008/0119839 | A1 | 5/2008 | Vancalette |
| 2008/0183167 | A1 | 7/2008 | Britva et al. |
| 2008/0287943 | A1 | 11/2008 | Weber et al. |
| 2009/0012585 | A1 | 1/2009 | Karni et al. |
| 2009/0171424 | A1 | 7/2009 | Britva et al. |
| 2009/0281537 | A1 | 11/2009 | Britva et al. |
| 2010/0036295 | A1* | 2/2010 | Altshuler ............... A61F 7/00 601/6 |
| 2010/0081971 | A1 | 4/2010 | Allison |
| 2010/0114007 | A1 | 5/2010 | Fischer et al. |
| 2010/0286673 | A1 | 11/2010 | Altshuler |
| 2011/0313411 | A1* | 12/2011 | Anderson ............... A61F 7/00 606/25 |
| 2012/0041525 | A1 | 2/2012 | Karni et al. |
| 2012/0071794 | A1 | 3/2012 | Karni |
| 2012/0123319 | A1 | 5/2012 | Britva et al. |
| 2012/0330194 | A1 | 12/2012 | Britva et al. |
| 2014/0007895 | A1 | 1/2014 | Britva et al. |
| 2014/0135662 | A1 | 5/2014 | Britva et al. |
| 2015/0045857 | A1 | 2/2015 | Britva et al. |
| 2015/0080991 | A1 | 3/2015 | Britva et al. |

FOREIGN PATENT DOCUMENTS

| | | |
|---|---|---|
| EP | 1797847 | 6/2007 |
| EP | 1797847 A1 | 6/2007 |
| EP | 2201917 | 6/2010 |
| EP | 2201917 A1 | 6/2010 |
| EP | 2272455 | 1/2011 |
| EP | 2272455 A1 | 1/2011 |
| GB | 2286660 | 8/1995 |
| GB | 2286660 A | 8/1995 |
| JP | S60-137359 | 7/1985 |
| JP | 04-133822 | 12/1992 |
| JP | 10-052475 | 2/1998 |
| JP | 2006-130055 | 5/2006 |
| JP | 2006130055 A | 5/2006 |
| JP | 2009-240795 A | 10/2009 |
| JP | 2010-536499 | 12/2010 |
| KR | 20-0431404 | 11/2006 |
| KR | 10-0802155 | 2/2008 |
| RU | 2074680 | 3/1997 |
| RU | 2074680 C1 | 3/1997 |
| WO | WO 2003/078596 | 9/2003 |
| WO | WO 2003/078596 A2 | 9/2003 |
| WO | WO 2005/096979 | 10/2005 |
| WO | WO 2006/066226 A1 | 6/2006 |
| WO | WO2006066226 | 6/2006 |
| WO | WO 2006/127467 | 11/2006 |
| WO | WO 2007/064718 | 6/2007 |
| WO | WO2008055243 | 6/2007 |
| WO | WO2008055243 | 5/2008 |
| WO | WO 2008/091983 | 7/2008 |
| WO | WO2008083305 | 7/2008 |
| WO | WO 2009/026471 | 2/2009 |
| WO | WO 2009/146053 | 12/2009 |
| WO | WO 2010/017477 | 2/2010 |
| WO | WO 2010/075448 | 7/2010 |
| WO | WO2013075006 | 5/2013 |
| WO | WO2013075016 | 5/2013 |

OTHER PUBLICATIONS

Lewis, Thomas, "The Blood Vessels of the Human Skin," The British Medical Journal, pp. 61-62; Jul. 10, 1926.
Third Chinese Office Action for Chinese Application No. 201280064282.0 dated Jan. 16, 2017.
English translation of Notice of Reasons for Rejection dated Sep. 4, 2017 for Japanese Application No. 2016-223046.
Israeli Office Action dated Oct. 30, 2017 for Israeli National Phase Application No. 232670.
The Chinese Office Action for Chinese Application No. 201280064282.0 dated Sep. 16, 2015.
Chinese Office Action and Search Report for Chinese Application No. 201280064282.0 dated May 24, 2016.
Communication and European Search Report for European Application No. 12850035 dated Jul. 3, 2015.
International Written Opinion for International Patent Application No. PCT/US2012/065664 dated Mar. 14, 2013.
International Search Report for International Patent Application No. PCT/US2012/065664 dated Mar. 14, 2013.
U.S. Appl. No. 60/886,587, filed Jan. 25, 2007, Bryan Weber.
U.S. Appl. No. 61/041,593, filed Apr. 1, 2008, Dieter Manstein.
U.S. Appl. No. 61/174,004, filed Apr. 30, 2009, Karni.
Israeli Office Action for Israeli Patent Application No. 211109 dated Jun. 19, 2012.
European Search Report for European Application No. 09805610.4 dated Aug. 2, 2012.
Chinese Office Action for Chinese Patent Application No. 200980134959.1 dated Mar. 29, 2013.
The Second Office Action for Chinese Patent Application No. 200980134959.1 dated Jul. 17, 2014.
International Search Report and Written Opinion for International Application No. PCT/US2009/053153 dated May 11, 2010.
International Search Report and Written Opinion for International Application No. PCT/US2012/065643 dated Mar. 14, 2013.

(56) References Cited

OTHER PUBLICATIONS

Har-Shai, Y. et al., "Effect of skin surface temperature on skin pigmentation during contact and intralesional cryosurgery of keloids," J. Eur Acad Dermatol Vener. 21(2):2007.
Notice of Final Rejection dated Aug. 23, 2019 for Korean national phase application No. 10-2014-7016426.
Summary of Notice of Reasons for Rejection dated Aug. 5, 2019 for Japanese national phase application No. 2016-223046.
Communication pursuant to Article 94(3) EPC dated Jun. 21, 2018 for European patent application No. 12850035.2.
Notice of Grounds for Rejection dated Apr. 3, 2020 for Korean patent application No. 10-2019-7034799.
Notice of Grounds for Rejection dated Oct. 17, 2018 for Korean Patent Application No. 10-2014-7016426.
Notice of Grounds for Rejection dated Apr. 14, 2020 Issued for Korean Patent Application No. 10-2019-7034799.
Notice of Final Rejection dated Feb. 15, 2021 issued for Korean Patent Application No. 10-2019-7034799.
First Chinese Office Action dated Nov. 4, 2020 issued for Chinese Application No. 201811171613.6.

\* cited by examiner

METHOD AND APPARATUS FOR CRYOGENIC TREATMENT OF SKIN TISSUE

CROSS-REFERENCE TO RELATED APPLICATION(S)

The present application is a continuation of U.S. National Phase application Ser. No. 14/358,359 filed May 15, 2014, which will issue as U.S. Pat. No. 9,974,684 on May 22, 2018 and relates to and claims the benefit and priority from International Patent Application No. PCT/US2012/065643 filed Nov. 16, 2012, which claims the benefit of priority from U.S. Provisional Patent Application No. 61/560,621 filed on Nov. 16, 2011, the entire disclosures of which is are incorporated herein by reference in their entireties.

FIELD OF THE DISCLOSURE

The present disclosure is directed to a cosmetic method and apparatus for improving skin appearance. More specifically, the present disclosure is directed to exemplary embodiments of such method and apparatus adapted to cool and/or freeze skin tissue to affect pigmentation, e.g., to lighten the appearance of the skin.

BACKGROUND INFORMATION

Controlled freezing of biological tissue, such as skin tissue, can produce various effects. Certain tissue freezing procedures and devices, such as conventional cryoprobes, can cause severe freezing of tissue and generate cellular damage. It has been observed that moderate degrees of freezing can produce particular effects, such as affecting the expression of skin pigmentation.

There is a demand for cosmetic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as large freckles, 'café au lait' spots, melasma, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas are typically located within the epidermis; however, they can also result from excess melanin deposited within the dermis. Many topical formulations are being marketed that claim to lighten age spots and reduce the effects of such hyperpigmentation. However, these cosmetic formulations may have questionable effectiveness.

Hypopigmentation of skin tissue has been observed as a side effect in response to temporary cooling or freezing of the tissue, such as may occur during cryosurgery procedures. Loss of pigmentation following skin cooling or freezing may result from decreased melanosomes production, destruction of melanocytes, or inhibited transfer of melanosome into the keratinocytes in the lower region of the epidermal layer. The resultant hypopigmentation may be long-lasting or permanent. It has also been observed that some of these freezing procedures can generate regions of hyperpigmentation of skin tissue.

Accordingly, there may be a need to provide methods and apparatus that can provide controlled freezing of skin or other tissue, and gradual lightening of skin tissue that can address and/or overcome at least some of the deficiencies or issues described herein above.

SUMMARY OF EXEMPLARY EMBODIMENTS

The herein described exemplary embodiments pertain to a cosmetic method and apparatus. Synergetic effects may arise from different combinations of the features and embodiments described herein, although all such combinations might not be described in detail. Further, it shall be noted that all exemplary embodiments of the present disclosure concerning a method, might be carried out with the order of the steps as described, nevertheless this has not to be the only and essential order of the steps of the method. All different orders and combinations of the method steps are herewith described.

Exemplary embodiments of the present disclosure relate to non-invasive methods and apparatus for controlled cooling and freezing of skin tissue, which can reduce an overall pigmentation of an area of skin using cryogenic techniques. In one exemplary embodiment of the present disclosure, an apparatus can be provided for cooling or freezing small or discontinuous regions of skin to produce a lightening of the skin appearance.

According to an exemplary embodiment of the present disclosure, the apparatus can include a plurality of protrusions, e.g., short columns or tapered objects, preferably formed of a material having a large thermal effusivity, e.g., an effusivity at least 10 times greater than that of skin tissue. For example, the protrusions can be made at least partially of a metal or alloy, such as brass, gold, silver, copper, or the like, diamond or diamondlike carbon, a frozen material, or another material that has a high thermal effusivity. The protrusions can be attached or mechanically and/or thermally to a base, which can also be formed at least partially of a material having a high heat capacity and/or large thermal diffusivity or effusivity. In certain exemplary embodiments, the base and protrusions can be formed from a single material. An insulated handle or cover can be provided for the base. The exemplary apparatus can be placed in a freezer such that the protrusions are cooled to subzero temperatures, and then positioned such that the tips of the protrusions contact an area of skin to be treated.

In further exemplary embodiments of the present disclosure, the base of the apparatus can include one or more reservoirs or ducts. A refrigerant or other heat-absorbing medium, such as a saline solution, a water-alcohol mixture, a water-glycol mixture, or the like can be provided in the reservoir to cool the plate. Optionally, a cooled refrigerant can be circulated through the reservoir and/or the one or more ducts that may be formed in the base to provide continuous cooling to the base and attached protrusions.

In another exemplary embodiment of the present disclosure, a Peltier device or other cooling device or source can be provided in thermal contact with the base and/or the protrusions to cool the plurality of protrusions.

In still further exemplary embodiments of the present disclosure, the protrusions have a distal portion and a proximal portion, wherein the distal portion of the protrusions can be configured to contact the skin surface. At least the distal portion or end of the protrusions may be formed using a material having a high thermal conductivity, such as diamond, gold, copper, or the like. The width or diameter of the distal portion or end of the protrusions or cold objects configured to contact the skin can be greater than about 2 mm, greater than about 5 mm, or as large as about 20 mm.

The average separation distance between these distal ends can be, e.g., approximately the same as the width or diameter of the regions, or somewhat less than this width or diameter, e.g., about one-half or one-fourth of the width or diameter, or smaller. Thus, the diameter values described above can also correspond to separation distances or multiples thereof in certain herein disclosed embodiments of the present disclosure. Such sizes of the distal ends and separation distances can be sufficiently large to facilitate rapid, reliable and/or controllable cooling of regions of skin tissue while allowing presence of less-cooled or unfrozen regions between the portions of skin contacted by the protrusions or cold objects, which can generate a more controlled overall pigmentation effect in the skin.

The total area and/or length of the distal portions of the protrusions configured to contact the skin tissue can be less than proximal portions of the high-conductivity material that are in thermal communication with the base or other thermal mass. For example, the total area and/or length of the distal ends can be less than about 0.8 times the area and/or length of the proximal portion of the high-conductivity material. This ratio of areas facilitates small portions of skin contacting the distal ends of the protrusions to be in an efficient thermal communication with a larger area of the base or other thermal mass that is provided at a lower temperature, which can provide more rapid and effective local cooling of the skin portions.

In a further exemplary embodiment of the present disclosure, an apparatus can be provided that include a plurality of thermally conductive arrangements that are in thermal communication with a base. An insulating material can be provided between the thermally conductive arrangements such that the distal ends of the thermally conductive arrangements are substantially coplanar with a lower surface of the insulating material. This exemplary apparatus can provide extraction of heat from spatially separated regions of skin tissue through the thermally conductive arrangements and into the base while inhibiting or preventing significant heat extraction from areas of tissue between these spatially separated regions. The sizes and separation distances of the distal ends of these thermally conductive arrangements can be substantially the same as the dimensions described above for the distal portions or ends of the protrusions or cold objects.

In a further exemplary embodiment of the present disclosure, a cosmetic method can be provided to produce hypopigmentation in skin tissue. Such method can be used on various parts of the skin, including the face, neck, hands, arms, legs, or torso. In one exemplary embodiment, the method for lightening the appearance of skin can be provided that includes cooling and/or freezing a plurality of small skin regions to induce localized hypopigmentation effects. The individual areas that are cooled or frozen can have a minimum dimension along the skin surface of greater than about 2 mm, or greater than about 5 mm, or even greater than about 8 mm. Larger areas can also be cooled or frozen. A maximum dimension along the skin surface of these individual areas that are cooled or frozen can be about 20 mm, 15 mm, or 10 mm. Such sizes of separated cooled or frozen regions area can be small enough to provide a gradual overall lightening, while being large enough to facilitate stability and controllability of the cooling or freezing process. Further lightening can be achieved by treating a particular region of skin more than once.

In a still further exemplary embodiment of the present disclosure, the cosmetic method can include freezing regions of skin tissue using a plurality of thermally conductive arrangements or cold objects such as, e.g., tip portions of an array of cold protrusions or a plurality of thermally conductive protrusions, to reduce and/or eliminate expression of pigmentation in the frozen regions. The width or diameter of the cold objects configured to contact the skin to generate the frozen regions can be greater than about 2 mm, greater than about 5 mm, or as large as about 20 mm. The average separation distance between these cooled or frozen regions can be, e.g., approximately the same as the width or diameter of the regions, or somewhat less than this width or diameter, e.g., about one-half or one-fourth of the width or diameter of the cold objects. Thus, the diameter values described above can also correspond to separation distances in certain herein disclosed embodiments of the present disclosure.

In a still further exemplary embodiment of the present disclosure, the cosmetic method can include freezing regions of skin tissue, for example, to at least the depth of the basal layer, e.g., to at least about the depth of the dermal-epidermal junction, which can provide a hypopigmentation effect. This freezing can preferably be achieved by contacting the skin surface with the cold objects that are provided at a temperature of about −5 degrees Celsius or colder, e.g., between about −7 and −10 degrees Celsius. In certain embodiments, temperatures as low as about −15 to −20 degrees Celsius can be used. Cooling times, which can correspond to the duration that the cold objects are contacted with the skin surface after local tissue freezing begins, can be less than about two minutes, or preferably less than about one minute, e.g., between about 30 seconds and 1 minute when the temperature of the cold objects are between about −7 and −10 degrees Celsius. Shorter cooling times can be used when the cold objects are provided at colder temperatures, e.g. less than about 30 seconds or even less than about 15 seconds when the temperature of the cold objects are between about −15 to −20 degrees Celsius. Such temperatures and times can lead to hypopigmentation responses in skin tissue while being fast enough to facilitate sequential cooling of a plurality of regions of skin. The above cited features regarding minimum dimensions, maximum dimensions, separation distances, and cooling times can be arbitrarily combined by a skilled practitioner without departing from the disclosure of the present disclosure.

One or more temperature and/or optical sensors, can be provided to control temperature of the cold objects, to detect the local temperature of contacted/cooled tissue, and/or to detect local freezing of skin tissue while the cold objects are placed in contact with the skin surface. Treatment time can be determined relative to the initiation of freezing, e.g., as a duration of contact time between the cold objects and the skin surface after local tissue freezing has begun. Temperature can be measured using contact sensors, non-contacting sensors, or both. A heating arrangement can optionally be provided to warm the frozen tissue after the particular treatment time has elapsed. A feedback signal may be generated and sent to the cooling device such that undesired or excessive cooling is avoided. In other words, a feedback control can be provided to ensure a safe treatment procedure for which no danger or risk results for the person undergoing the treatment.

According to further exemplary embodiments of the present disclosure, a method and apparatus for detection of tissue freezing at the onset of such freezing is provided. Such freezing detection, which can include temperature control and/or feedback, optical detection, and/or measurement of electrical and/or mechanical impedance of the skin tissue, will be described in more detail hereinafter.

This exemplary method can provide gradual lightening of the skin area being treated by forming very small depigmented areas without forming individual depigmented spots that may be apparent to the naked eye. Multiple treatments can be used to lighten the area further. The exemplary methods and apparatus described herein may also improve the general appearance of the skin by stimulating a response in the small regions of frozen tissue.

It shall further be noted that the herein described cosmetic method has been tested, and is a safe and routine procedure that can be practiced in beauty parlors or other settings. The presented method is a non-invasive a method. Moreover, the method is safe as it is non-invasive, does not present a substantial health risk, and does not require professional medical expertise to be performed. No clinician is needed to perform the embodiments of the method described herein, and no risk, much less a health risk, is presented for a person being treated with said cosmetic method, as will become clear from the following description.

These and other objects, features and advantages of the present disclosure will become apparent upon reading the following detailed description of embodiments of the invention, when taken in conjunction with the appended claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the exemplary embodiments of the present disclosure, in which.

Figure 1:
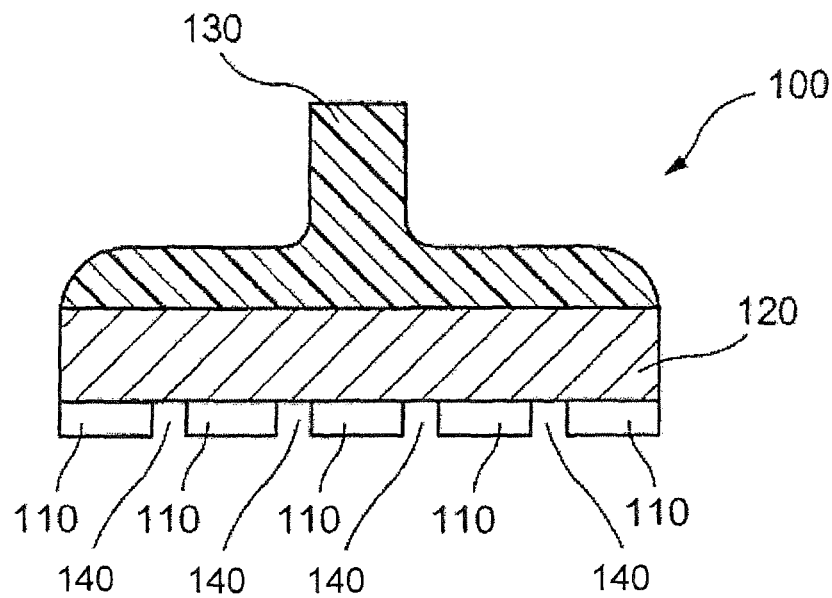
FIG. 1 is a side view of a first exemplary apparatus that can be used to produce a hypopigmentation cryogenically in a skin tissue according to an exemplary embodiment of the present disclosure.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

According to an exemplary embodiment of the present disclosure, a "fractional cryotherapy" approach can be used to controllably and non-invasively freeze small regions of skin tissue. Such freezing can lighten the overall appearance of the skin, or reduce the overall darkness of certain skin areas that have excess pigmentation. Small regions of skin can be contacted with cold objects to inhibit formation and/or expression of pigment in the underlying skin. This exemplary effect can provide long-lasting or permanent lightening of the areas being treated.

FIG. 1 depicts an exemplary apparatus 100 for controllably freezing skin, e.g., to produce controlled amounts of hypopigmentation in skin tissue, in accordance with exemplary embodiments of the present disclosure. The exemplary apparatus 100 can include a plurality of protrusions 110 attached to a base 120. The protrusions 110 can be provided in a thermal communication with the base 120. A plurality of gaps 140 can be provided between the protrusions 110. In certain exemplary embodiments, the protrusions 110 and the base 120 can be formed from a single material. A handle 130, which can be formed of an insulating material such as plastic, can be affixed to the base 120 to facilitate handling and positioning of the apparatus 100. The apparatus 100 shown in FIG. 1 is not necessarily drawn to scale. For example, the general dimensions of the base 120, protrusions 110, and gaps 140 are not limited to the proportions illustrated in the FIG. 1. In one exemplary embodiment, the base 120 can be provided as a plate or substrate that is relatively thin from top to bottom as compared to the lateral dimensions, for example, having a length to thickness ratio that is greater than about 3:1, or greater than about 5:1, or even greater than about 10:1. In further exemplary embodiments, the relative width and length of the protrusions 110, and the width of the gaps 140 between them, can be varied as described herein.

The protrusions 110 can be formed from a metal or a metal alloy, or another material having a much higher thermal effusivity than the skin tissue, e.g. at least 10 times the thermal effusivity of skin. For example, the protrusions 110 can be made of brass, copper, silver, aluminum, graphite, diamond, diamondlike carbon, other materials which are used in conventional contact cryoprobes, or combinations thereof. The base 120 can be formed from the same material or another material having similar thermophysical properties. For example, materials having a much higher thermal conductivity than the skin tissue can be used to facilitate an extraction of heat from the portion of the tissue contacted by the cooled protrusions 110. Further, materials having a much higher thermal effusivity than the skin tissue, e.g. at least 10 times the thermal effusivity of skin, can be held at a cold temperature, and extract heat from the portion of tissue contacted by the cooled protrusions 110. The distal ends of the protrusions 110 can be substantially flat and/or slightly rounded or convex to provide good thermal contact with skin tissue when the apparatus 100 can be placed on the area of the skin to be treated.

In one exemplary embodiment, the protrusions 110 can be formed of a metal such as copper, silver, or aluminum. A layer or coating of diamond, diamondlike carbon, or another material having a higher thermal effusivity than the material of the protrusions 110, can be optionally provided on the distal ends of the protrusions 110. For example, diamond and diamond like carbon have very high thermal effusivities, and a layer of one of these materials on the distal ends of the protrusions 100 can improve thermal transfer between the cooled protrusions 110 and the skin being treated.

A cold environment can be provided to cool the apparatus 100 to a particular temperature. For example, the exemplary apparatus 100 can be placed in a refrigerated enclosure, e.g., a freezer compartment, to cool the protrusions 110 and the base 120 to a particular temperature. Alternatively, the protrusions 110 and/or the base 120 can be cooled by spraying them with a refrigerant such as liquid nitrogen, or immersing them in a cold bath, such a chilled solution of alcohol and water or a cold saline solution. Preferably, the bath can be maintained at a predetermined temperature. After cooling, the distal ends of the protrusions 110 can then be pressed against an area of skin to be lightened for a predetermined time, which can locally chill and/or freeze a plurality of spots within the area. For example, the protrusions 110 and the base 120 can preferably be cooled to at least −5 degrees Celsius or colder, e.g., between about −7 and −10 degrees Celsius, or even as cold as −15 to −20 degrees Celsius, so that the protrusions 110 can cool skin tissue sufficiently and freeze at least a portion of the skin tissue when the apparatus 100 is brought into contact with the skin surface, which can also produce a hypopigmentation response.

In a further embodiment, a skin freezing system can be provided that includes the apparatus 100 and the above-described cold environment, such as a refrigerated enclosure, a cold bath containing a chilled solution or a slush, a conduit circulating cold liquid or gas, or the like. The cold environment can be configured to cool or pre-cool the apparatus 100 to a particular temperature. In further embodiments, a system can be provided that includes such a cold environment and any of the exemplary apparatuses described herein, where the cold environment can be configured to cool or pre-cool at least a portion of such apparatus.

Figure 2:
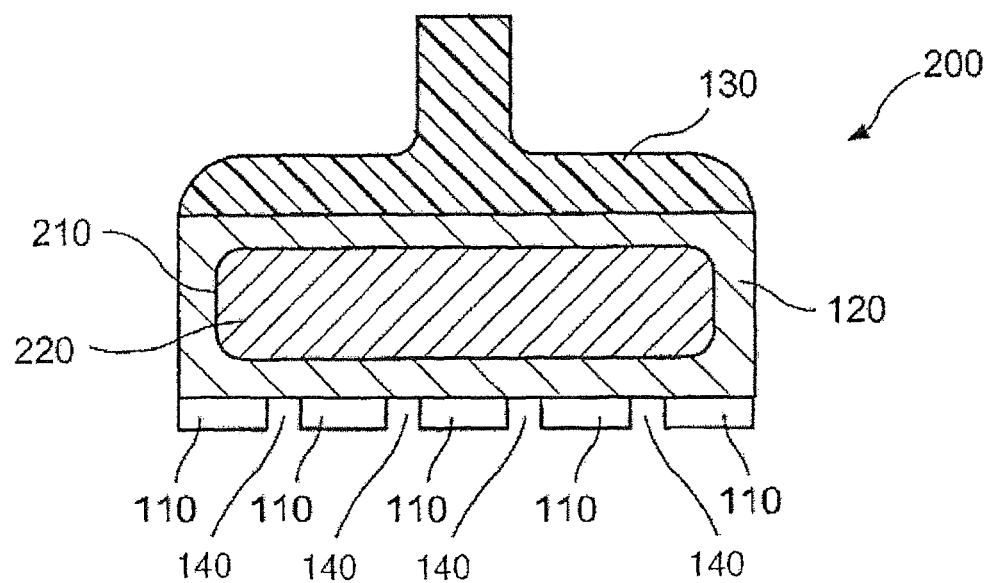
FIG. 2 is a side cross-sectional view of a second exemplary apparatus that can be used to produce the hypopigmentation cryogenically in the skin tissue according to an exemplary embodiment of the present disclosure.

In a further exemplary embodiment shown in FIG. 2, an apparatus 200 can be provided that is similar to the exemplary apparatus 100 shown in FIG. 1. The base 120 of the apparatus 200 can include a hollow reservoir 210 which contains a refrigerant 220. The refrigerant 220 can be a material that freezes, for example, at a temperature below 0 degrees Celsius. Such a refrigerant 220, when frozen in the reservoir 210, can facilitate cooling of the base 120 and/or the protrusions 110 at colder temperatures for a longer period of time. A maximum dimension along the skin surface of these individual areas that are cooled or frozen can be chosen from the group consisting of 25 mm, 20 mm, 15 mm, or 10 mm.

In certain exemplary embodiments of the present disclosure, the refrigerant 220 can be selected such that it exhibits a solid-liquid phase change at a particular temperature or a temperature range, for example, at least as cold as about −5 degrees Celsius, e.g., between about −5 or −7 degrees and −10 degrees Celsius, or optionally as cold as about −15 to −20 degrees Celsius. For example, when the exemplary apparatus 200 warms up to the phase change temperature (if it is initially colder), the refrigerant 220 can facilitate a maintenance of the base 120 and/or the protrusions 110 at approximately the phase change temperature or within a particular phase change temperature range for an extended period of time (e.g., during longer contact periods between the protrusions 110 and the skin tissue being treated, or during application of the apparatus 200 to a plurality of regions of skin being treated). Heat extracted from the skin tissue can be conducted through the protrusions 110 and the base 120 to the refrigerant 220, which can absorb the heat at a relatively constant temperature as the phase change in the refrigerant 220 progresses. This exemplary arrangement can facilitate a predictable and repeatable rate of heat transfer flow from the skin contacting the protrusions 100 because the temperature difference provided by the apparatus 200 can be maintained substantially constant. This exemplary embodiment can also provide cooling and/or freezing of the upper portion of the skin tissue at a particular temperature or within a narrow range of temperatures, e.g., between about −5 or −7 degrees Celsius and about −10 or −20 degrees Celsius.

A thermal conduction between the distal ends of the protrusions 110 and the base 120 can be improved if the protrusions 110 have a large aspect ratio (e.g., the ratio of the width or diameter of the protrusions 110 to the length of such protrusions 110 extending from the bottom of the base 120). For example, the aspect ratio can be greater than unity, or preferably greater than about 2. Such a large aspect ratio can improve thermal conduction between the distal ends of the protrusions 110 and the base 120, such that the distal ends of the protrusions 110 can be maintained closer to the cold temperature of the base 120 and be less likely to warm up significantly when contacting the skin tissue. The length of the protrusions 110 can be long enough to prevent the base 120 from directly contacting the skin surface, but short enough to provide a good thermal communication between the distal ends of the protrusions 110 and the base 120.

For example, the length of the protrusions 110 extending from the lower surface of the base 120 can be less than about 1 cm, or less than about 5 mm. Such a short protrusion length can facilitate heat flow between the distal ends of the protrusions 110 which are placed in contact with the skin tissue being treated and the base 120, by providing a shorter path for heat flow. Accordingly, heat can be extracted more rapidly from the regions of the skin contacting the distal ends of the protrusions 110, facilitating faster and more efficient local freezing of the tissue. The protrusions 110 can be long enough such that the lower surface of the base 120 does not contact the surface of the skin when the distal ends of the protrusions 110 are placed against the skin surface.

The diameter or width of the distal end of each protrusion 110 can be greater than at least about 2 mm, or greater than about 5 mm. In certain exemplary embodiments of the present disclosure, this diameter or width can be about 8 mm or more, e.g., as large as 20 mm. Larger widths of the protrusions 110 can facilitate faster local cooling of the skin tissue and/or improved control of the protrusion temperature, e.g., based on the larger thermal mass and/or improve thermal conductance between the base 120 and the distal ends of such larger protrusions 110, while still cooling or freezing relatively small discontinuous areas of the skin, which may provide an overall moderated visual pigmentation effect. This can facilitate faster treatment times to achieve a desired extent and/or duration of local cooling or freezing of the skin tissue, as described herein. Such larger protrusion widths can also facilitate placement of various sensors, e.g., optical or resistive sensors, on, at, or proximal to the distal ends of the protrusions 110 as described herein, while avoiding significant impairment of heat conduction through the protrusions 110.

Figure 3A:
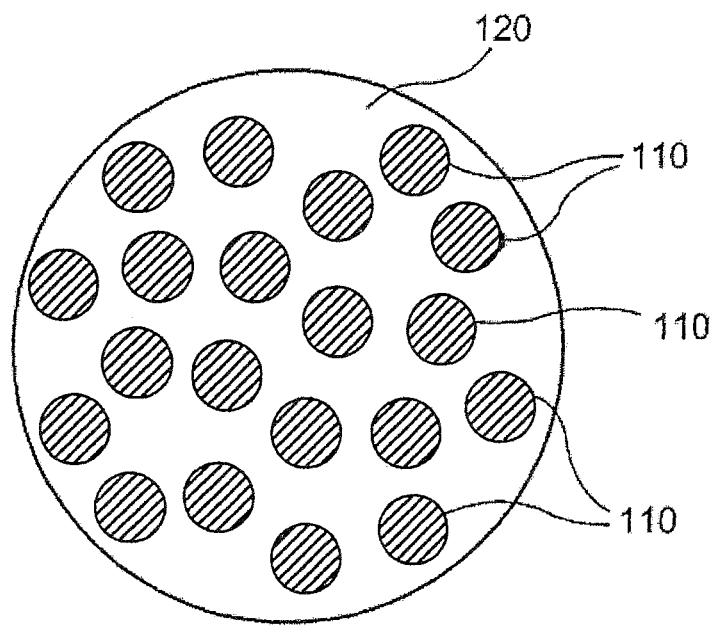
FIG. 3A is a bottom view of a first exemplary configuration of protrusions that can be used to produce the hypopigmentation in the skin tissue according to an exemplary embodiment of the present disclosure.

An exemplary array of distal ends of the protrusions 110 protruding from the base 120 is shown in FIG. 3A, in a bottom view of the exemplary apparatus 100 or 200. The distal ends of the protrusions 110 in this embodiment can be provided with an approximately circular shape. An irregular (e.g., random or semi-random) arrangement of the protrusions 110 can be provided, as shown in FIG. 3A. Such an irregular array can provide reduced clustering of the treated regions and an appearance of more uniform depigmentation, e.g., if the exemplary apparatus 100 shown in FIG. 1 or the exemplary apparatus 200 shown in FIG. 2 is applied a plurality of times to a single area of the skin in different orientations. In further embodiments, the protrusions 100 can be arranged in a uniform square array, a uniform hexagonal array, or the like.

Figure 3B:
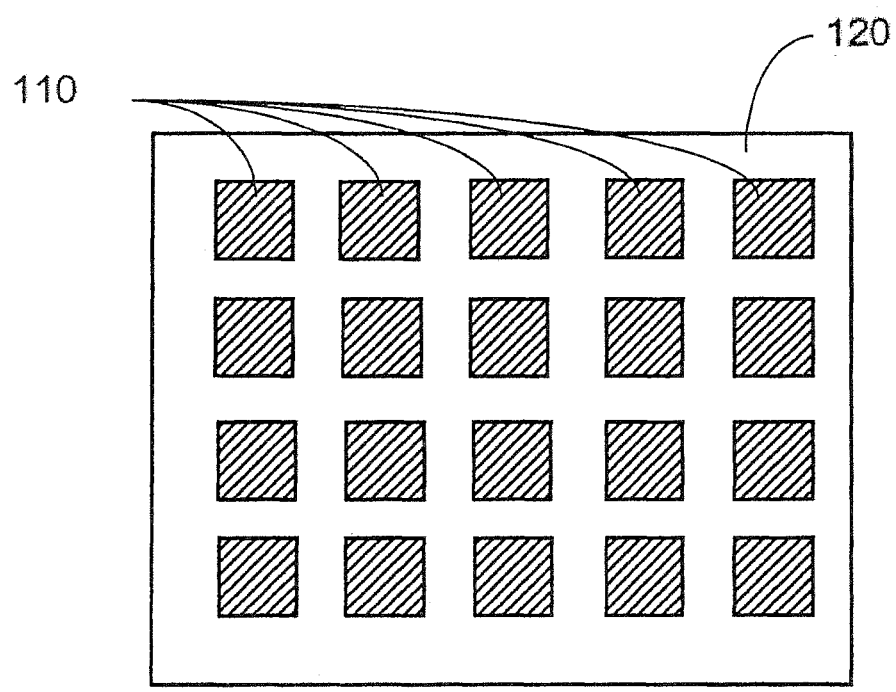
FIG. 3B is a bottom view of a second exemplary configuration of the protrusions that can be used to produce the hypopigmentation in the skin tissue according to an exemplary embodiment of the present disclosure.

In a further exemplary embodiment, illustrated in FIG. 3B, the distal ends of the protrusions 110 provided on the bottom of the base 120 can be provided with a substantially square or rectangular shape. In a still further embodiment, shown in FIG. 3C, the distal ends of the protrusions 110 are provided as elongated rectangles that are substantially parallel, with gaps provided between them.

Figure 3C:
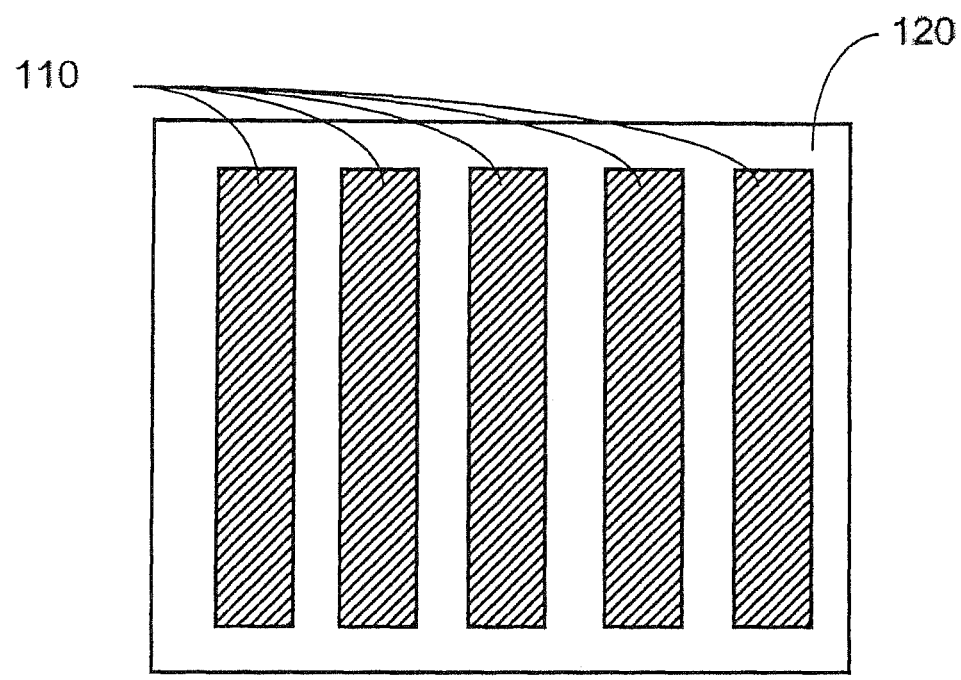
FIG. 3C is a bottom view of a third exemplary configuration of the protrusions that can be used to produce the hypopigmentation in the skin tissue according to an exemplary embodiment of the present disclosure.

The cross-sectional shape can refer to the shape of a section that is substantially parallel to the lower surface of the base 120 and/or substantially parallel to the skin surface when the protrusions 110 are contacting the skin surface. Various cross-sectional shapes may be provided for the protrusions 110 in embodiments of the present disclosure. For example, cross-sectional shapes of the distal ends of the protrusions 110 can be round, square, or rectangular, as shown in FIGS. 3A, 3B, and 3C, respectively. Other cross-sectional shapes can be provided such as hexagonal, ovoid, irregular, and the like. Further, the cross-sectional shape of the protrusions 110 may vary between the proximal end contacting the base 120 and the distal end that is configured to contact skin tissue, e.g., varying from round to ovoid or square to round, etc.

Figure 3D:
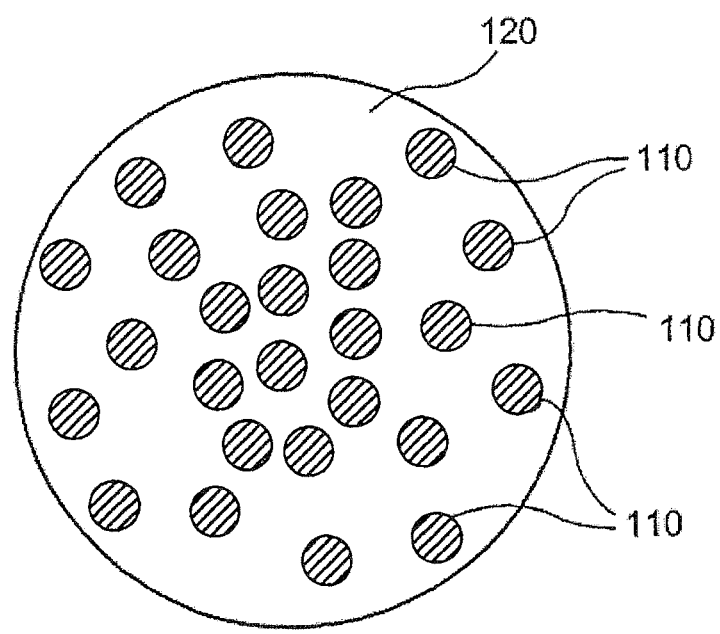
FIG. 3D is a bottom view of a fourth exemplary configuration of the protrusions that can be used to produce the hypopigmentation in the skin tissue according to an exemplary embodiment of the present disclosure.

The protrusions can be provided in a substantially uniform areal density, as shown in FIGS. 3A-3C. This uniform spacing corresponds to a substantially uniform distance between adjacent protrusions 110 over the bottom surface of the base 120. In further embodiments, the average spacing and/or the width of the protrusions 110 can vary over the bottom surface of the base 120. For example, a plurality of substantially round protrusions 110 are shown in FIG. 3D, with the protrusions 110 being closer together near the center of the base 120 and further apart and/or having smaller widths near the outer perimeter of the base 120. Such a "feathered" arrangement of the protrusions 110 can facilitate more uniform treatment of a larger area and provide a smoother transition from darker to lightened skin.

For example, if the apparatus 100 or 200 is sequentially placed on adjacent regions of skin (with the duration of each placement sufficient to achieve the desired effect as described herein), feathering of the protrusions 110 near the edges of the base 120 can provide a more uniform pattern of cooled areas if there is some overlap between adjacent placements of the exemplary apparatus 100, 200. The density of the cooled regions (e.g., those regions of skin surface that contact the distal ends of the protrusions 100) may be increased somewhat in the overlapping areas because they have been exposed to two or more placements of the apparatus 100, 200. However, the edge portions of the base 120 that are placed in contact with the skin can have a lower density of protrusions 110, such that overall density of cooled regions in the overlapped treatment areas may be increased relative to this lower density. Such increased density may be comparable to the higher density of protrusions 110 near the central portion of the base 120. Accordingly, the reduced density or increased spacing of the protrusions 110 near the perimeter of the base 120 can help to avoid excessive cooling in the overlap regions. Such feathering of the protrusions 110 near the outer portions of the base 120 can be achieved, e.g., by increasing average spacings between adjacent protrusions 110 as shown in FIG. 3D, and/or by reducing the average size of the distal ends of the protrusions 110 near the outer portions of the base 120 relative to the distal end sizes in the central portion of the base 120.

The distance between distal ends of the adjacent protrusions 110 can be comparable to their diameter or width, or somewhat smaller. For example, the average distance between the distal ends of the adjacent protrusions 110 can be, e.g., about the same as an average diameter or width of the distal ends, or about one-half of this average width or less. For example, yet smaller distances between the distal ends of the adjacent protrusions 110 can also be used, e.g., distances less than about one-quarter of the distal end widths or less. These exemplary configurations, distal end sizes, and separation distances between the distal ends can facilitate a formation of spatially separated depigmented portions of the tissue that may have substantially unaffected tissue between them. This can provide a gradual lightening of the area of the tissue being treated, while the size of the distal ends of the protrusions 110 can facilitate control and increase stability of the cold temperatures during the cooling procedure and/or facilitate placement of sensors proximal to the protrusions 110.

The exemplary sizes, spacings, and configurations of the distal ends of the protrusions 110 described herein can provide controlled cooling or freezing, and subsequent depigmentation, of regions of skin while maintaining pigmented areas between the frozen regions to produce an overall lightening of the skin appearance.

The cross-sectional shape of the base 120 shown in FIGS. 3A and 3D is substantially circular, whereas the shape of the base 120 shown in FIGS. 3B and 3C is substantially square. Other shapes and combinations of shapes may also be used in accordance with further embodiments of the present disclosure. For example, the cross-sectional shape of the base 120 can be elliptical or oval, square, rectangular, or irregular. The particular shape of the base 120 can be selected based on the area being treated. For example, an elongated crescent-shaped base 120 can be used to lighten bags under the eyes.

The size of the base 120 can also be selected based on the size of the area being treated. For example, depigmentation of small areas can be achieved using a relatively small base 120 having few protrusions 110. Larger bases 120 having more protrusions 110 can be provided to treat larger areas of the skin with a single application, and reduce the overall treatment time for larger areas of skin that require multiple placements of the apparatus against adjacent skin treatment areas. The protrusion sizes and spacings can be provided as described herein for various sizes of the base 120.

In general, the number and configuration of the protrusions 110 may be selected to provide appropriate patterns of depigmented spots for particular treatments. For example, devices having just the few closely-spaced protrusions 110 (e.g., less than about 10 or 15 protrusions 110 where, e.g., the spacing between the distal ends thereof are about, e.g., 1-2 times the width of these distal ends) can be used for lightening small age spots. Larger numbers of the protrusions 110 can be provided on a larger base 120 to lighten larger areas of skin with a single treatment.

The exemplary apparatus 100 or the exemplary apparatus 200 can be cooled, for example, by placing the entire apparatus in a freezer and/or by exposing it to another cold material or environment. The protrusions 110 can be cooled to a temperature at which they can induce contact freezing in skin tissue. The base 120 can also cooled to the same temperature. The cooled base 120 can provide a thermal sink or reservoir that can help maintain the protrusions 110 at or close to the cooled temperature while portions of the apparatus 100 (e.g., distal ends of the protrusions 110) are in contact with skin tissue.

Figure 4A:
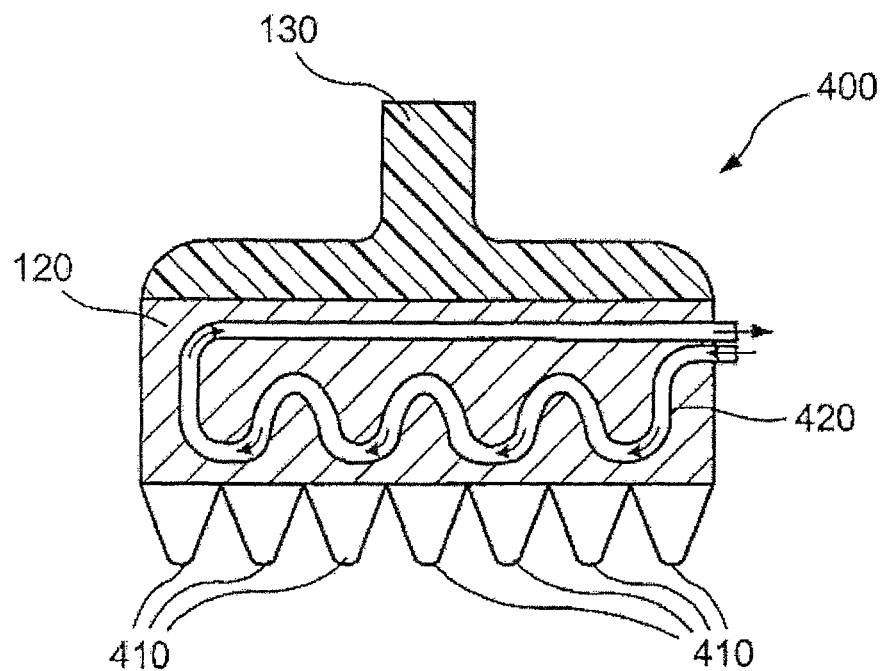
FIG. 4A is a side cross-sectional view of a third exemplary apparatus that can be used to produce the hypopigmentation cryogenically in the skin tissue according to an exemplary embodiment of the present disclosure.

In a further exemplary embodiment of the present disclosure, an exemplary apparatus 400 can be provided as shown in FIG. 4A. The base 120 of the exemplary apparatus 400 can include one or more channels 420 therethrough. A cooled refrigerant can be circulated through the channels to cool the base 120 and the protrusions 410, and optionally to maintain them at a particular temperature. For example, a conventional fluid pump (not shown) can be used to circulate a cooling medium through the channels 420 in the base 120. Such pump can be located remotely from the apparatus 400, or in certain embodiments it can be affixed to the apparatus 400. The refrigerant can also be provided in a reservoir (not shown) that can be insulated and/or actively cooled using conventional techniques. The apparatus can further include a thermal control arrangement configured to maintain a particular temperature of the refrigerant, e.g., using one or more temperature sensors provided in communication with an active cooling arrangement. The reservoir can also be located remotely from the apparatus 400, or it can be affixed thereto in further embodiments.

The protrusions 410 can be tapered as shown in FIG. 4A, such that the cross-section area varies along the length of the protrusions 410. They can be formed using a material having a large thermal conductivity as described herein. For example, the protrusions 410 can have a conical or pyramidal shape, or the like. The diameter or width of the proximal ends of the protrusions 410 can be, e.g., at least twice the width or diameter of the distal ends thereof. Such tapered shapes can provide efficient thermal communication between the distal ends of the protrusions 410 and the cooled base 120. For example, the tapered protrusions 410 can facilitate an extraction of heat from a small region of the tissue contacting the distal end of the protrusions 410 through a larger area of the base 120 that is in thermal communication with the proximal end of the protrusions 410.

Figure 4B:
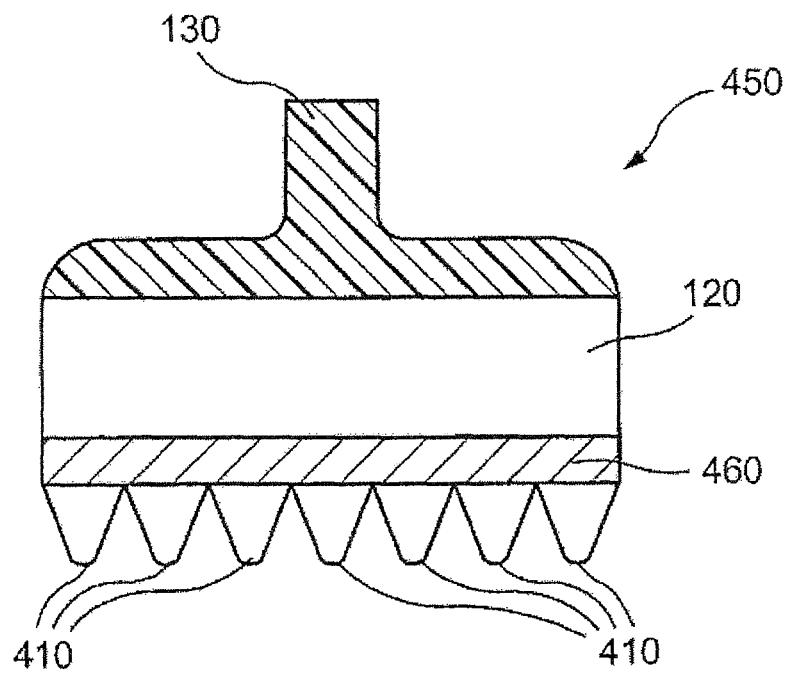
FIG. 4B is a side cross-sectional view of a fourth exemplary apparatus that can be used to produce the hypopigmentation cryogenically in the skin tissue according to an exemplary embodiment of the present disclosure.

In yet another exemplary embodiment of the present disclosure, an exemplary apparatus 450 can be provided as shown in FIG. 4B. A layer 460 of material having a high thermal conductivity can be affixed to a lower surface of the base 120 and provided in a good thermal contact therewith. The layer 460 can be provided, for example, as a plate, or as a film deposited on the lower surface of the base 120. The protrusions 410 can be tapered as described herein, and provided in thermal contact with the layer 460. Alternatively, the layer 460 and the protrusions 410 can be formed as a single component from a high conductivity material, e.g., brass, aluminum, diamond, or the like. Similar to the exemplary apparatus 400 shown in FIG. 4A, the tapered protrusions 410 can facilitate the extraction of heat from a small region of tissue contacting the distal end of the protrusions 410 that are in thermal communication with a larger area of the base 120 through the protrusions 410 and the plate 460.

Figure 5:
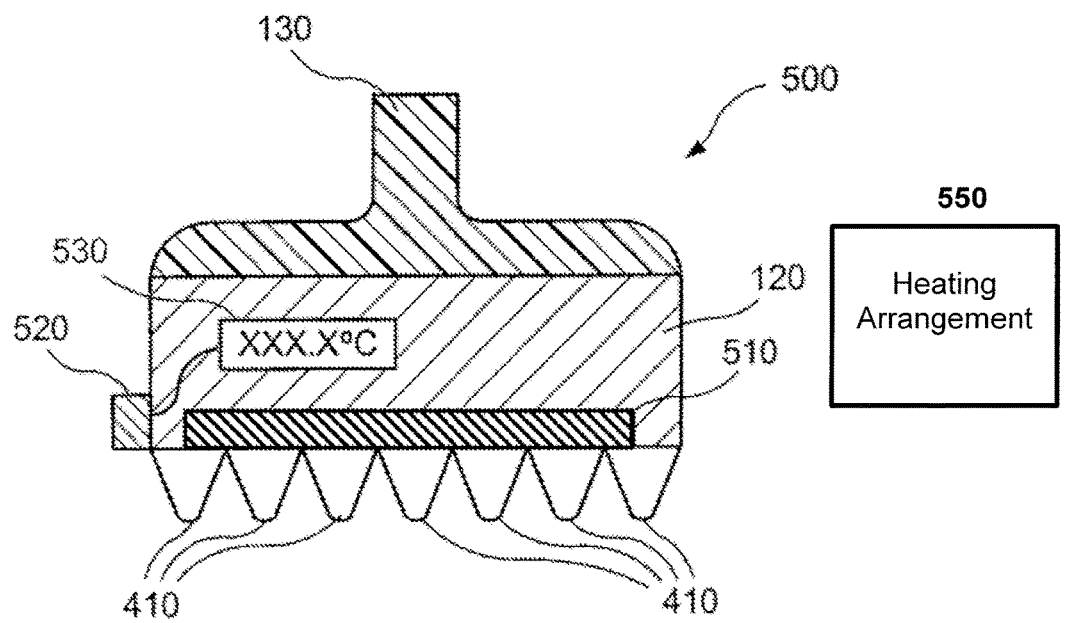
FIG. 5 is a side cross-sectional view of a fifth exemplary apparatus that can be used to produce the hypopigmentation cryogenically in the skin tissue according to an exemplary embodiment of the present disclosure.

In a still further embodiment of the present disclosure, an exemplary apparatus 500 can be provided as shown in FIG. 5. The base 120 can include one or more Peltier devices 510 configured to cool a portion of the apparatus 500, e.g., to a particular temperature. The cold side of the Peltier device 510 can be provided in thermal contact with the protrusions 410 and/or the lower portion of the base 120. A power source for powering the Peltier device 510 can be provided as part of the apparatus 500, or alternatively an external power source can be provided separate therefrom. The upper or warm side of the Peltier device 510 can be cooled by contacting it with a cooled object, by allowing or directing air or another gas to flow over at least a portion of it, and/or by other conventional cooling or ventilation techniques.

A temperature sensor 520 can be provided proximal to the lower portion of the base 120 or the protrusions 410. The temperature sensor can include, e.g., one or more thermocouples or thermistors or the like. Such temperature sensor 520 can be connected to a display 530 to indicate the temperature of the apparatus 500 near the protrusions 410. The temperature sensor 520 can also be connected to the Peltier device 510 or any other active cooling arrangement as part of a control system to maintain the base 120 and/or protrusions 410 at or near a predetermined temperature. In other words, a feedback control can be provided based on the sensor 520 to ensure that no danger results for the person undergoing the treatment. Thus, a feedback signal may be generated and sent to the cooling device such that undesired or excessive cooling is avoided. This may provide for a highly safe treatment. Wire-based communication or wireless communication may be provided between components of the apparatus of the present disclosure. This will be explained in more detail with regards to FIGS. 6 and 8 hereinafter.

Figure 6:
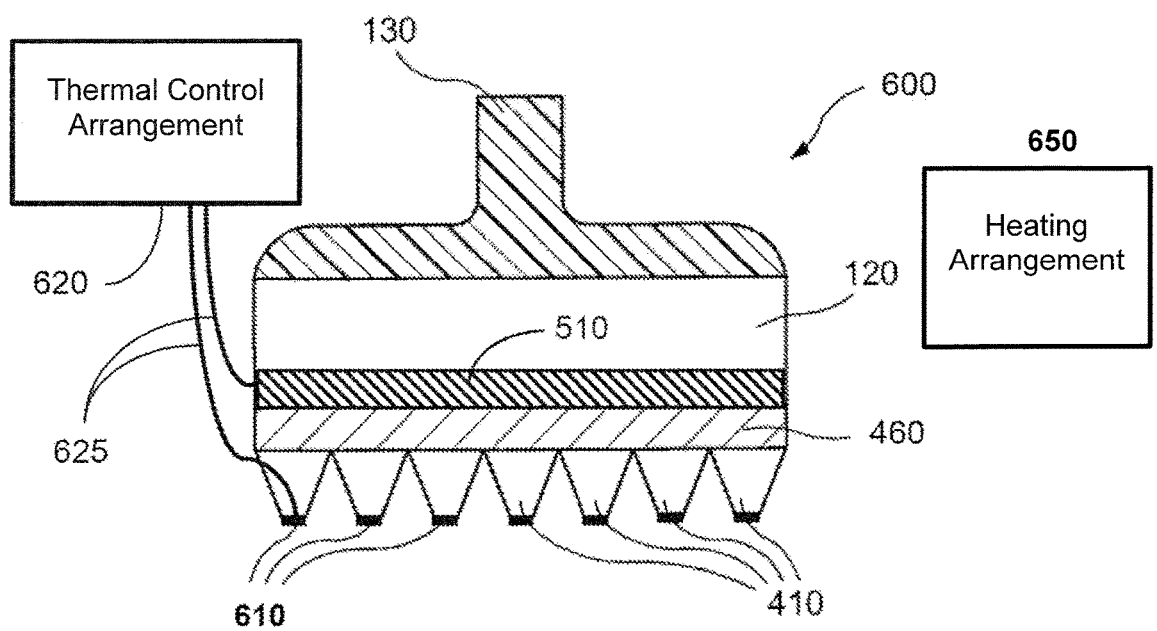
FIG. 6 is a side cross-sectional view of a sixth exemplary apparatus that can be used to produce the hypopigmentation cryogenically in the skin tissue according to an exemplary embodiment of the present disclosure.

In yet another exemplary embodiment, an exemplary apparatus 600 shown in FIG. 6 can be provided that include a base 120, an optional handle 130, a plurality of thermally conductive protrusions 410 that are in thermal communication with a thermally conductive layer or plate 460. The protrusions 410 and plate 460 can optionally be formed form as a single unit, e.g., by molding, grinding, or etching the protrusion shapes from a single piece of metal or the like. A cooling arrangement, e.g., a Peltier device 510, a controlled-temperature reservoir 210 or channels 420 circulating a refrigerant (not shown), or the like, can be provided in thermal communication with the plate 460 and/or protrusions 410. One or more thermal sensors 610 can be provided on or near the distal end of one or more protrusions 410. For example, the thermal sensor 610 can include a thermistor, a thermocouple, a resistance temperature detector (RTD), or the like.

One or more temperature sensors 610 can be provided on the distal end of one or more protrusions 410. The temperature sensor 610 can cover a portion of this distal end, which can reduce the effect of the mass and material of the sensor on local heat transfer between the distal end and the skin surface. Alternatively, the sensor can be configured to cover substantially all of the distal end of the protrusion 410, which can provide a more stable and/or accurate signal, and can also have a more predictable effect on the local heat transfer. In certain embodiments, the thermal sensor 610 can be embedded in or provided with a material having a high thermal conductivity that covers substantially all of one or more of the distal ends. In further embodiments, one or more sensors 610 can be provided or mounted proximal to the distal end of one or more protrusions 410. In these exemplary configurations, the sensors 610 may detect a composite temperature that depends on both the local protrusion temperature and the skin surface temperature when the apparatus 600 is placed on the skin.

Wires 625 or other communication arrangements can be provided between the temperature sensors 610 and a thermal control arrangement 620, and between the thermal control arrangement 620 and the cooling arrangement. The wires 625 can be passed through a portion of the protrusions 410 and/or the plate 460, or optionally can be routed between the protrusions 410, e.g. proximal to the plate 460, or both. The thermal control arrangement 620 can be provided external to the apparatus 600, or it can be mounted on or within the apparatus 600, and can optionally be integrated with the cooling arrangement 510. Optionally, a wireless communication between the sensor 610 and the thermal control arrangement 620 can be provided within this embodiment. Consequently, the thermal control arrangement 620 in combination with the sensor or sensors 610 can provide for a temperature feedback control based on temperatures detected at the end of the protrusions 410. This may increase the safety of the apparatus and the corresponding method.

The thermal control arrangement 620 can be configured to control characteristics of the operation of the cooling arrangement, e.g., based on signals received from the one or more thermal sensors 610. For example, the thermal control arrangement 620 can be configured to detect signals from the temperature sensors 610 and to vary the power characteristics provided to the Peltier device 510 if present (e.g., turn power on/off, reduce/increase power, and/or alter the duty cycle characteristics of the power) based on these signals. The thermal control arrangement 610 can be configured to use a proportional, integral, and/or derivative feedback algorithm to control the operation of the Peltier device 510, e.g., to maintain the distal ends of the protrusions 410 at a predetermined temperature or to approximate a predetermined temperature profile over time. Such control algorithms are known in the art. The thermal control arrangement 620 and sensors 610, as described above, can also be provided and used with the other cooling arrangements described herein, e.g., by controlling temperature of the reservoir 210 (if present) or controlling refrigerant temperature and/or circulation rate through channels 420 (if present), or by controlling temperature of still other types of cooling arrangements known in the art.

Further, the thermal control/processor arrangement 620 may be configured to control the cooling arrangement based on a received temperature signal and to modify or affect at least one parameter of the cooling arrangement such as set-point temperature, cooling time, cooling pulse duration, number of protrusions that are cooled, flow rate and/or temperature of a refrigerant, or any combination thereof.

It has been observed that cooling the basal layer of the skin (e.g., proximal to the dermal-epidermal junction) by cooling a surface of the skin to a particular temperature for a particular treatment time (which can be determined as a time interval that begins when local freezing of tissue begins). Accordingly, any of the apparatuses described herein can be configured to provide one or more surfaces (e.g. the cooled protrusions 110, 410, 610) at a temperature of about −5 degrees Celsius or colder, e.g., between about −5 degrees and −10 degrees Celsius, or preferably between about −7 to −10 degrees Celsius. Treatment times corresponding to these temperatures can be, e.g., less than about one minute, for example, about 45 seconds to one minute, or as short as about 30 seconds or less in some embodiments. Such combinations of temperatures and times that generate freezing in tissue can produce hypopigmentation effects in skin without producing depigmentation (i.e., total pigmentation loss).

In further exemplary embodiments, the temperature of the cooled protrusions 110, 410, 610 can be can be colder than −10 degrees Celsius, e.g., as cold as −15 or −20 degrees Celsius, with correspondingly shorter contact or treatment times, to generate sufficient local cooling and freezing of the tissue without inducing undesirable tissue damage from excessive cooling. For example, treatment times can be as short as 15 seconds or less, e.g., about 5 seconds, at these temperatures of between about −15 and −20 degrees Celsius. Such colder temperatures can be used, for example, to facilitate faster treatment times, and/or to compensate for such effects as thermal inefficiencies in the heat conduction through the distal ends of the cooled protrusions 110, 410, 610 and/or warming effects of the skin that may be heated by local blood flow.

The temperature can preferably be low enough to locally freeze at least a portion of the epidermal layer of the skin tissue proximal to the distal ends of the cooled protrusions 110, 410, 610 for a particular time interval when these distal ends are brought into contact with the area of the skin to be treated. The distal ends of the protrusions 110, 410, 610 can be placed in contact with the region of the skin being treated for a duration of time sufficient to generate subsequent hypopigmentation of the frozen regions. This time duration may be determined as a time interval following initiation of local freezing of the skin tissue. Inducing local freezing of the upper layers of skin tissue (e.g., down to the basal layer) at these temperatures can also improve the hypopigmentation response. Portions of the upper dermal layer can also be frozen. Inducing local freezing of the upper layers of skin tissue (e.g., down to the basal layer) at these temperatures can also improve the hypopigmentation response. The treatment time can preferably be not so long as to cause excessive freezing and issue damage in the cooled or frozen tissue. Accordingly, the time of contact can be selected without excessive experimentation to provide portions of skin tissue between the regions of skin contacted by the cooled protrusions that do not undergo a significant degree of hypopigmentation based on the cooling or freezing of nearby tissue. For example, if the distal ends of the protrusions 110, 410, 610 are maintained at a temperature of between about −5 and −10 degrees Celsius, a contact time between about 30 and 60 seconds may be sufficient to induce local freezing of the skin surface region that can lead to hypopigmentation. In general, an appropriate time of contact can be determined based on the geometry, materials, and initial cooled temperature of the exemplary embodiments of the apparatus described herein. In general, the time and temperature used can be selected to produce a small zone of frozen tissue proximal to each of the protrusions 110, 410, 610 and maintain it for a particular duration, while maintaining unfrozen skin tissue in a portion of the skin tissue therebetween.

In certain exemplary embodiments, the material and size (e.g., diameter, shape and length 115) of the protrusions 110, 410, 610 can be selected such that the corresponding apparatus is initially cooled, and the protrusions 110, 410, 610 gradually warm up during prolonged contact with skin tissue. Accordingly, the protrusions 110, 410, 610 can be provided in contact with the skin for longer periods of time, and gradual warming of the protrusions 110, 410, 610 can prevent excessive freezing of the regions of skin proximal thereto.

Figure 7A:
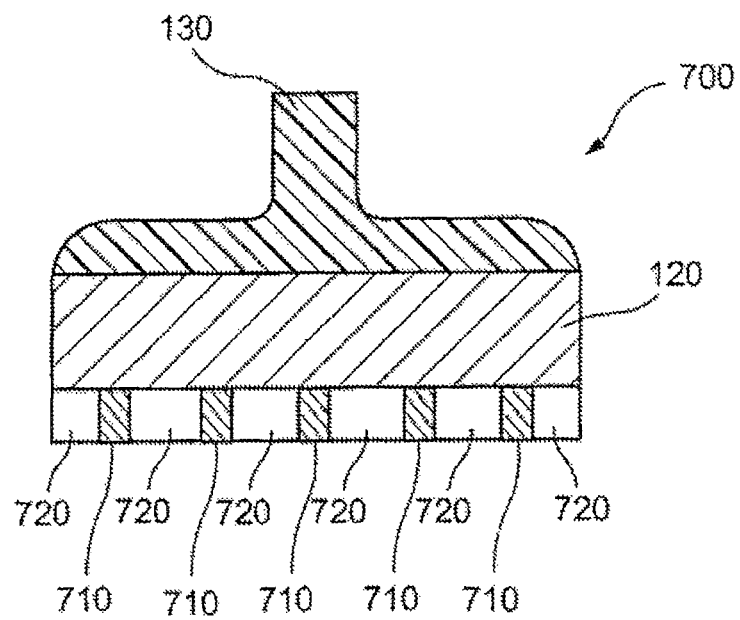
FIG. 7A is a side cross-sectional view of a seventh exemplary apparatus that can be used to produce the hypopigmentation cryogenically in the skin tissue according to an exemplary embodiment of the present disclosure.

FIG. 7A depicts a further exemplary apparatus 700 for producing controlled amounts of cooling or freezing to generate or induce hypopigmentation in skin tissue in accordance with exemplary embodiments of the present disclosure. The exemplary apparatus 700 can include a plurality of thermally conductive arrangements 710 and an insulating material 720 provided between at least a portion of the thermally conductive arrangements 710. The thermal material 720 can be provided, e.g., in a form of a sheet of material with holes provided through the sheet that the thermally conductive arrangements 710 can pass through. Alternatively, the thermal material 720 can be provided as a foam or a curable material, e.g., a curable or setting foam or polymer, or other pliable material that can be formed or cast in place.

The conductive arrangements 710 can be formed at least in part using the materials having a high thermal conductive and/or high specific heat capacity as described herein for the protrusions 110. The conductive arrangements 710 can be provided in a thermal communication with the base 120 or with other components of the apparatus 700. In certain exemplary embodiments, the conductive arrangements 710 and at least a portion of the base 120 can be formed from a single material. The conductive arrangements 710 can be cooled using any of the procedures or arrangements in the various exemplary embodiments described herein. For example, the conductive arrangements 710 can be provided in thermal communication with a cooling plate 460 as shown, e.g., in FIGS. 4B and 6, or the conductive arrangements 710 and cooling plate 460 can be formed from a single piece of thermally conductive material (e.g., a metal or metal alloy) as described herein. Cooling arrangements such as the conduit 420 shown in FIG. 4A or the Peltier device 510 illustrated in FIGS. 5 and 6 can also be used in further exemplary embodiments. A handle 130 can be affixed to the base 120 to facilitate handling and positioning of the apparatus 700.

A lower surface of the exemplary apparatus 700 can be substantially flat, or it may have a curved or contoured shape configured to correspond to a particular area of skin to be treated. This lower surface may be placed against an area of skin to be treated. The distal ends of the conductive arrangements 710 may then contact spatially separated regions of the skin tissue to cause local cooling or freezing of these regions, as described in detail herein. The insulating material 720 can provide a thermal barrier that reduces or inhibits extraction of heat from the skin tissue between the distal ends of the conductive arrangements 710.

The size, shape, arrangement and/or spacings of the distal ends of the conductive arrangements 710 may include any of the corresponding parameters for distal ends of the protrusions 110 described in detail herein. The thickness of the insulating material 720 (and length of the conductive arrangements 710) can be large enough to provide sufficient thermal isolation of the skin surface between the conductive arrangements 710 to prevent substantial cooling or freezing thereof. The thickness of the insulating material 720 and length of the conductive arrangements 710 can also be small enough to facilitate efficient extraction of heat from the regions of skin tissue through the conductive arrangements 710.

Figure 7B:
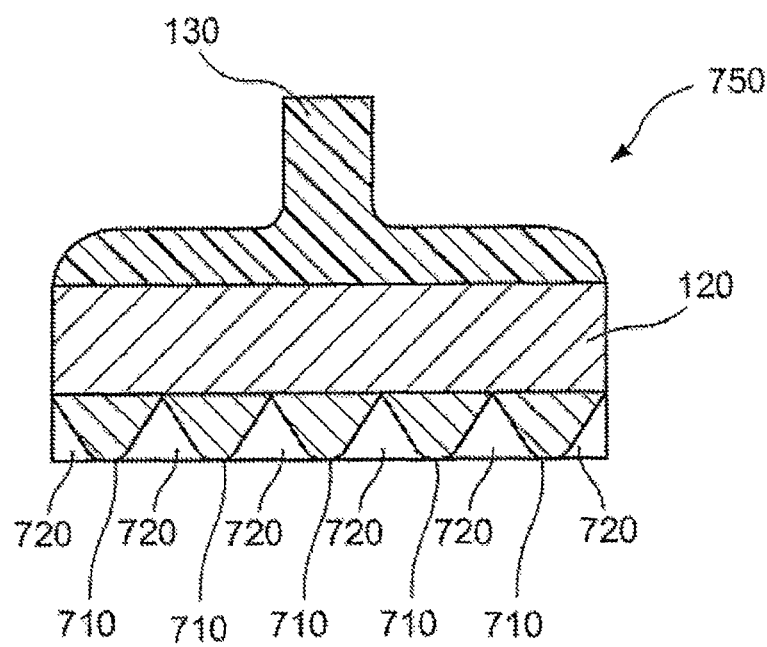
FIG. 7B is a side cross-sectional view of an eighth exemplary apparatus that can be used to produce the hypopigmentation cryogenically in the skin tissue according to an exemplary embodiment of the present disclosure.

FIG. 7B depicts a further exemplary apparatus 750 in accordance with certain exemplary embodiments of the present disclosure, which is similar to the exemplary apparatus 700 shown in FIG. 7A. The thermally conductive arrangements 710 in the exemplary apparatus 750 can be provided with a tapered shape, such that the areas of the proximal ends of the conductive arrangements 710 that are in direct thermal contact with the base 120 are larger than the areas of the distal ends that may be placed in direct contact with the surface of the skin tissue. Such a tapered geometry can facilitate more efficient conduction of heat away from the spatially separated regions of skin tissue through the conductive arrangements 710 and into the cooled base 120. This effect of a tapered shape on heat conduction is described in more detail herein with respect to the tapered protrusions 410 shown in FIGS. 4A and 4B. An insulating material 720 can be provided between at least a portion of the tapered conductive arrangements 710 to reduce an amount of heat extraction from the skin tissue between the distal ends of the conductive arrangements 710, as described above with respect to the exemplary apparatus 700. Various cooling arrangements and other features described herein may also be used with the exemplary apparatus 750.

Figure 8:
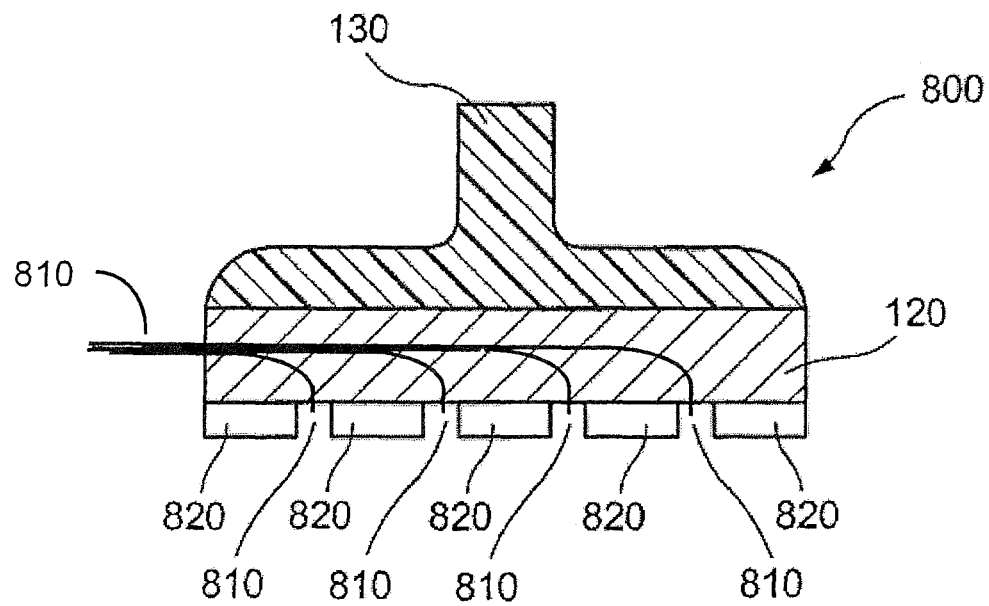
FIG. 8 is a side cross-sectional view of a ninth exemplary apparatus that can be used to produce the hypopigmentation cryogenically in the skin tissue according to an exemplary embodiment of the present disclosure.

Hypopigmentation effects based on contact cooling of the skin surface with one or more cold protrusions, as described herein, can be more effective if a local volume of tissue proximal to the surface is frozen. Cooling of the skin tissue, even when achieved by contacting the skin surface with protrusions cooled to below 0 degrees Celsius, e.g., cooled to about −5 to −10 degrees Celsius or colder as described herein, may not always lead to local tissue freezing. Such cooling procedures may instead lead to locally supercooled tissue that does not freeze. An apparatus 800 that can facilitate detection of tissue freezing during the cooling procedure is illustrated in FIG. 8.

The exemplary apparatus 800 can include a plurality of protrusions 820 provided on a lower surface of a base 120. The protrusions 820 can be cooled using any of the procedures or arrangements in the various exemplary embodiments described herein such as, e.g., those illustrated in FIGS. 1, 2, 4A, 4B, and 5. A handle 130 can be affixed to the base 120 to facilitate handling and positioning of the apparatus 800. One or more optical conduits 810 can be provided in the apparatus 800, wherein distal ends of the optical conduits 810 can be located proximal to one or more of the protrusions 820. The optical conduit 810 can include, e.g., an optical fiber, a waveguide, or the like.

In certain embodiments, the distal end of one or more optical conduits 810 can be provided proximal to an edge of a protrusion 820, or at a distal end of a protrusion 820, e.g., by locating the distal portion of an optical conduit 810 within a small hole drilled through a portion of the protrusion 820 or using a similar configuration. If an insulating material 720 is provided between the protrusions 820, e.g., as illustrated in FIGS. 7A and 7B, the distal portion of one or more optical conduits 810 can be provided through the insulating material 720 such that the distal end is exposed at the lower surface of the insulating material 720. Other configurations of the optical conduits 810 can also be provided in further embodiments, where the distal ends of the optical conduits 810 are proximal to the skin surface and/or in optical communication with the skin surface (e.g., there is an unimpeded optical path between the distal end of the optical conduit 810 and the skin surface) when the bottom side of the apparatus 800 is placed against the skin.

To detect freezing of skin tissue during cooling procedures as described herein, the proximal end of at least one optical conduit 810 can be provided in communication with a source of light or other optical energy (not shown). LEDs or other light sources that emit red light having a wavelength between about 600 nm and about 800 nm can be used. Other wavelengths of light may also be used in further embodiments. For example, light sources that emit light in the near-IR range (e.g., light having a wavelength between about 800 nm and about 2000 nm) can also be used. Such near-IR light may be relatively insensitive to variations in melanin levels of the skin region being treated, and thereby can be used to detect freezing in a variety of skin types.

During the cooling procedure, light can be emitted from the distal end of the at least one optical conduit 810 onto a region of the skin surface beneath the apparatus 800. Light that is reflected and/or scattered by the skin can enter the distal end of at least one optical conduit 810 and directed through the optical conduit 810 to an optical detector (not shown), e.g., a conventional light meter, charge-coupled device (CCD), optical transistor or the like, which can be provided at a proximal end of the optical conduit 810. In further embodiments, cladding can be removed from other portions of the optical conduit 810 instead of or in addition to at the distal end thereof, to facilitate detection of light directed toward a circumferential portion of the optical conduit 810, thereby facilitating detection of light using other orientations of the optical conduit 810 relative to the skin.

An exemplary variation in the intensity or other characteristic of the optical light can indicate the occurrence of local tissue freezing. For example, in certain embodiments the optical conduit 810 used to detect scattered and/or reflected light can be the same as the optical conduit 810 used to direct light onto the skin surface, or positioned very close to the optical conduit 810 used to direct light, e.g., within about 1-2 mm. If tissue freezing occurs, local reflectance of impinging light can increase the amount of light received by the detecting optical conduit 810. Such an increase in an optical signal can be used to confirm freezing of skin tissue when the apparatus 800 is placed on the skin for a particular duration. In further embodiments, the optical conduit 810 can be provided with one or more polarizing elements to reduce or suppress specular reflections from the fiber end and tissue surface, which can provide a more sensitive detection of local tissue freezing.

In further exemplary embodiments, the optical conduits 810 used to provide and detect light can be spaced further apart, e.g., at a distance greater than 3-4 mm. If tissue freezing occurs, the reflectance of the tissue can increase and more light directed at the skin will be reflected back from the surface region, whereas less light will be scattered laterally through the tissue. Accordingly, a decrease in the detected light signal from such a more distant detecting optical conduit 810 can also indicate local freezing of the skin tissue.

Different configurations of optical conduits 810 can be provided in further embodiments to detect tissue freezing or to obtain more detail about the tissue freezing as described herein. For example, each of a plurality of the optical conduits 810 can be configured to both direct light onto the skin surface beneath the apparatus and detect light scattered or reflected by the skin tissue. A plurality of such optical conduits 810 (e.g., three or more) can be used to provide information on the depth of freezing of the tissue. Alternatively, a plurality of spaced-apart optical conduits 810 can be configured to either direct light onto the skin or detect light as described herein. The optical detector can be configured and calibrated to detect a threshold change in the optical signal level that indicates freezing proximal to the distal ends of one or more of the optical conduits 810. In certain embodiments, an indicator can be provided, e.g., an LED or light bulb, a sound generator, a digital display, or the like, to confirm the occurrence of tissue freezing while the apparatus 800 is held in contact with the skin surface.

In further exemplary embodiments, temperature sensors 610, e.g., such as those illustrated in FIG. 6, can be configured to detect the occurrence of local tissue freezing. For example, in a typical cooling procedure, the temperature detected by a temperature sensor 610 will correspond to the temperature of the cold protrusion 410 that it is in contact with. When the apparatus 600 is placed on the skin surface, the detected temperature will rise as the distal ends of the protrusions 410 are warmed slightly by the skin. As conductive cooling of the skin by the protrusions 410 proceeds, the measured temperature will then decrease. The rate and extent of such decrease can depend on several factors, e.g., the initial temperature, material, and geometry of the protrusions 610, the efficiency of the cooling arrangement used to cool the protrusions 410, etc. When tissue freezing occurs near the distal ends of the protrusions 410, a slight temporary increase in local temperature may be detected that arises from latent heat released during the freezing phase transformation. The detected temperature can then continue to decrease as further cooling of the frozen tissue proceeds. Accordingly, a "bump" detected in the temporal cooling curve by a temperature sensor 610 can also indicate the occurrence of local tissue freezing.

An exemplary study was performed to illustrate the use of optical sensors to detect the onset of freezing in tissue in accordance with embodiments of the present disclosure. A 20 mm×20 mm flat aluminum contact plate was cooled to a temperature of −7.5 degrees Celsius. Two 1-mm optical fibers were inserted into holes drilled in the plate, with one fiber configured to illuminate the cooled tissue and the second fiber configured to detect light from the tissue as described herein. The cooled plate was placed in contact with a shaved skin surface on the flank region of a female Sinclair pig for 60 seconds. A thermocouple was used to monitor the temperature at a contact point of the cooling plate and the skin surface. The detected light signal was also monitored and recorded during this cooling procedure.

Figure 9:
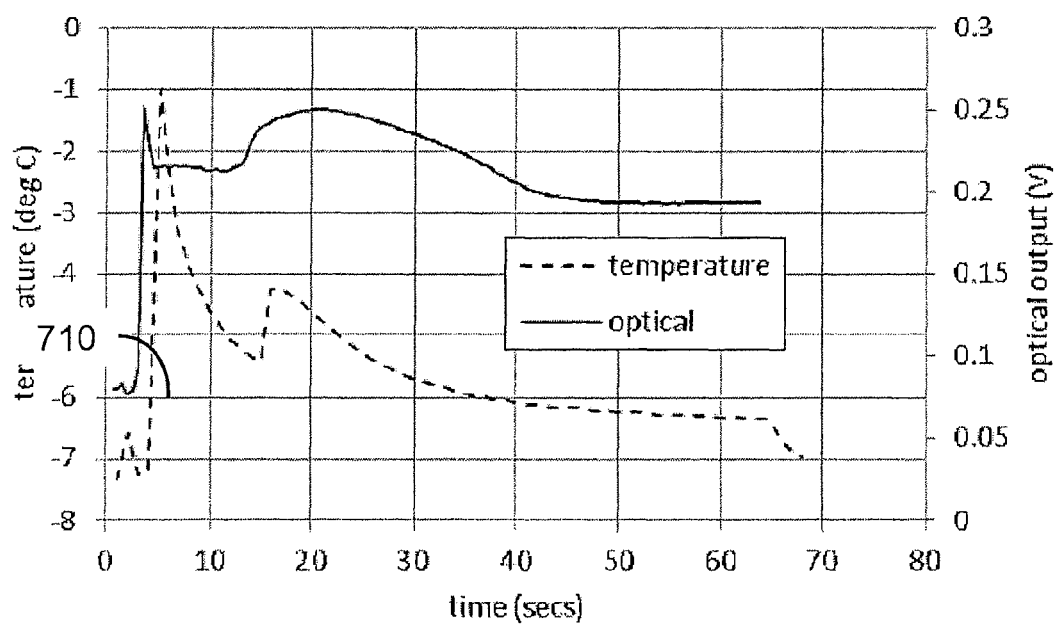
FIG. 9 is an exemplary data plot generated with an apparatus according to an exemplary embodiment of the present disclosure, the plot showing changes in both measured surface temperature and optical reflectance when a region of live pig skin is cooled and local freezing of the skin commences.

An exemplary set of data for this cooling procedure is shown in FIG. 9. The measured temperature (indicated by a dashed line in FIG. 9) was initially observed to rise rapidly (at about 5-6 seconds) when the initially cooled plate was brought into contact with the warmer skin surface. The temperature then dropped as the plate cooled the adjacent skin by thermal conduction. This cooling occurred between about 6 and 15 seconds in the data plot shown in FIG. 9. The optical output (measured in volts using an optical transistor, and indicated by a solid line in FIG. 9) remained fairly constant during this cooling process. At about 15 seconds, a small rise in temperature was detected, indicating the onset of local tissue freezing and release of a latent heat of freezing of the skin. This onset of tissue freezing was accompanied by an increase in the detected optical signal. The optical signal remained elevated as the frozen skin continued to cool. After the cooling plate was removed, it was confirmed that the surface region of the skin was frozen. This study demonstrates the use of optical sensors as described herein to detect the onset of tissue freezing based on a change in detected reflectance level when a skin surface is contacted by a cold object, and the use of temperature sensors to detect the onset of tissue freezing by the presence of a small plateau or transient rise in local temperature associated with a release of latent heat upon freezing.

In still further exemplary embodiments, sensors can be provided to facilitate detection of tissue freezing based on measurement of electrical or mechanical impedance. For example, electrical impedance has been shown to change with the onset of freezing in a number of materials including water and tissue. See, e.g., A. A. Gage, Cryobiology 16, pp. 56-62 (1979), B. Rubinsky, Ann. Rev. Biomed. Eng. 02, pp. 157-87 (2000), and T. H. Yu et al., Intl. J. Thermophysics, 24(2) (March 2003). In one embodiment, the electrical impedance can be measured between two or more locations along the bottom surface of the cooling plate 110 that is in contact with the skin surface. Alternatively, separate surface electrodes can be provided proximal to the cooled region and used to measure local electrical impedance of the skin. Such sensors for detecting electrical impedance of the skin can be used with any of the embodiments described herein. Alternatively or in addition, a force sensor can be provided to measure local mechanical impedance of the skin tissue. For example, force can be measured locally as a function of tissue displacement with such a force sensor. An accelerometer or some other sensor could also be used to measure a dynamic change in response to a low level impulse or dynamic event. Any of these types of exemplary sensors (thermal, optical, mechanical, force, etc.) can be used, either alone or in any combination, in the various embodiments of the invention described herein.

In still further exemplary embodiments, an indicating arrangement can be provided in communication with any of the sensors and apparatuses described herein that can be used to detect tissue freezing. Such an indicator can include, for example, an indicator light, a buzzer or other sound generator, a display panel, or the like. The indicating arrangement can be configured to provide a first signal to a user to indicate when tissue freezing has been detected. Such a signal can be used to determine the start of the desired treatment time. An exemplary timing arrangement can also be provided to indicate the time elapsed since the onset of local tissue freezing has been detected. Optionally, the timing arrangement can be configured to provide a second signal when a predetermined or preprogrammed time interval has passed since the onset of local freezing. This second signal can be used to indicate when the local cooling treatment has ended, and prompt a user to separate the apparatus used from contacting the skin surface. In further embodiments, the timing arrangement may only provide the second signal indicating when the apparatus should be removed from the skin, and not provide the first signal indicating the onset of local freezing.

The details of the present disclosure relating to detection of tissue freezing, temperature control, and/or process feedback based on, e.g., optical, electrical and/or mechanical properties and/or signals as illustrated in FIGS. 5, 6 8 and 9 and described above, may be implemented in all the other herein described embodiments of the present disclosure.

A heating arrangement 550, 660 (as shown in, e.g., FIGS. 5 and 6, respectively) can be provided with any of the exemplary apparatuses described herein. The heating arrangement 550, 660 can be used to warm and/or thaw the frozen tissue rapidly after a particular treatment time has elapsed, e.g., it can facilitate more precise control of local tissue freezing duration. Such a heating arrangement 550, 660 can include, e.g., an electrically resistive heating element provided on, within, or proximal to the cold surfaces of any apparatus described herein that is configured to contact and cool the skin. Alternatively, the heating arrangement can include a source of electromagnetic (EM) energy (e.g., a quartz lamp or other infrared emitter, a low-power laser, etc.) configured to direct such EM energy onto the cooled or frozen tissue and warm it by the process of energy absorption. The heating arrangement 550, 660 can also include one or more conduits proximal to the cold surfaces of any apparatus described herein that is configured to circulate a warm fluid and thereby warm the cold surfaces and adjacent cooled tissue. Other conventional heating arrangements can also be used, such as a source of moving warm air (e.g., an arrangement similar to a heat gun or a hair dryer) that can warm the tissue by convection. The heating arrangement 550, 660 can be used while the cooling apparatus is contacting the skin surface, or after the apparatus has been removed from the skin surface, depending on the type of heating arrangement and cooling apparatus used.

Multiple fractional cryotherapy treatments in accordance with any of the exemplary embodiments described herein can be performed on a particular area of the skin to produce further lightening of the skin. The multiple treatments can preferably be performed at longer intervals, e.g., days or weeks, to allow hypopigmentation effects from a particular treatment to become visually evident before subsequent treatments are performed. Such exemplary multiple treatments can be used to gradually lighten the skin appearance in the treated area. Because the depigmented spots are spatially separated, multiple treatments may be applied to a single area without producing discernible white spots.

In further exemplary embodiments of the present disclosure, a method can be provided for gradually and controllably lightening the appearance of skin tissue by generating hypopigmentation using cryogenic techniques. A plurality of spatially-separated small regions of the epidermal skin tissue can be cooled or frozen to induce hypopigmentation. The size of the spatially-separated frozen regions can be greater than about 2 mm, or more preferably greater than about 5 mm. Portions of the upper dermal layer beneath the frozen epidermal regions can also be frozen or cooled during such exemplary procedures.

The distance between adjacent frozen regions of skin can be greater than about 3 times the diameter or lateral dimension of the frozen regions along the tissue surface, or greater than about 5 times this diameter. These exemplary distance ratios can facilitate a preservation of unaffected and normally pigmented portions of skin between the frozen regions. Accordingly, the exemplary cryogenic hypopigmentation method(s) described herein can provide a gradual lightening of the area of skin being treated without producing readily discernible depigmented spots. Freezing of the skin tissue can be achieved by contact cooling, e.g., using an exemplary apparatus as described herein. Alternatively, such depigmentation can be produced by spraying a cryospray or applying a cold substance through a mask that protects certain regions of the skin surface being treated while allowing the cryospray to contact and freeze spatially-separated regions of the skin surface.

The exemplary procedures described herein can be repeated on a particular area of skin to further lighten it. Preferably, the interval between successive procedures can be long enough to allow the hypopigmentation effects to be visibly evident and to better control the overall degree of lightening obtained. Multiple procedures can also be repeated at shorter intervals if desired, for example, to provide a greater overall degree of hypopigmentation in a first area of skin as compared to a second area, using a particular apparatus having a particular size and spacing of protrusions to provide contact cooling.

Various combinations of the protrusion geometries and characteristics, cooling arrangements, temperature and/or freezing detectors, and other apparatus features described herein can also be used in further exemplary embodiments of the present disclosure, even where certain combinations may not be explicitly illustrated or described herein in single embodiments.

The foregoing merely illustrates the principles of the invention. Other variations to the disclosed embodiments can be understood and effected by those skilled in the art in practising the claimed invention from a study of the drawings, the disclosure, and the appended claims. In the claims, the word "comprising" does not exclude other elements or steps and the indefinite article "a" or "an" does not exclude a plurality. A single processor or other unit may fulfil the functions of several items or steps recited in the claims. The mere fact that certain measures are recited in mutually different dependent claims does not indicate that a combination of these measures cannot be used advantageously. A computer program may be stored/distributed on a suitable medium such as an optical storage medium or a solid-state medium supplied together with or as part of other hardware, but may also be distributed in other forms, such as via the Internet or other wired or wireless telecommunication systems. Any reference signs in the claims should not be construed as limiting the scope of the claims. Various modifications and alterations to the described embodiments will be apparent to those skilled in the art in view of the teachings herein. It will thus be appreciated that those skilled in the art will be able to devise numerous techniques which, although not explicitly described herein, embody the principles of the invention and are thus within the spirit and scope of the invention. All patents and publications cited herein are incorporated herein by reference in their entireties.

What is claimed is:

1. A method for freezing a skin tissue to produce hypopigmentation effects in the skin tissue, the method comprising:

freezing a portion of a skin tissue to produce hypopigmentation effects in the skin tissue portion with a non-penetrating cooling portion of a skin treatment device defining a treatment area that contacts a surface of the skin tissue, wherein a density of a cooling contact area is greater near a central region of the cooling portion treatment area than at a peripheral region of the cooling portion treatment area for blending treatment or avoiding excessive cooling in areas of an overlap between adjacent placements in the peripheral region.

2. The method of claim 1, wherein the cooling portion comprises a plurality of protrusions.

3. The method of claim 2, wherein the density of the plurality of protrusions decreases from the central region of the cooling portion toward the peripheral region of the cooling portion.

4. The method of claim 2, wherein a distal end size of the plurality of protrusions decreases from the central region of the cooling portion toward the peripheral region of the cooling portion.

5. The method of claim 1, further comprising cooling the cooling portion to a temperature between −5 and −20° C. to provide controlled heat removal from the skin tissue so as to locally control freezing of the skin tissue in less than 2 minutes during contact between the surface of the skin tissue and the cooling portion.

6. The method of claim 1, further comprising monitoring an elapsed time following a detection of an onset of the freezing of the skin tissue to prevent or reduce at least one of excessive freezing or tissue damage.

7. The method of claim 1, further comprising modifying a set-point temperature or cooling time of a cooling arrangement thermally coupled with the cooling portion based on a received temperature sensor signal.

8. The method of claim 1, further comprising detecting freezing of the skin tissue to avoid local supercooling of the skin tissue.

9. The method of claim 1, further comprising successively placing the skin treatment device on the surface of the skin tissue so there is at least one overlap region between adjacent placements, wherein the cooling contact area provides a feathered arrangement that avoids excessive cooling in the at least one overlap region.

10. The method of claim 1, further comprising facilitating handing and positioning of the skin treatment device with a handle.

11. The method of claim 1, wherein the skin tissue comprises an epidermal tissue.

12. The method of claim 6, further comprising outputting a signal to indicate when the onset of the freezing of the skin tissue has been detected.

13. The method of claim 6, further comprising outputting a signal after an elapse of a predetermined treatment time following the onset of the freezing of the skin tissue.

14. The method of claim 6, further comprising removing the cooling portion from the surface of the skin tissue after elapse of a predetermined treatment time following the onset of the freezing of the skin tissue.

15. The method of claim 6, wherein detection is carried out by an optical sensor, a temperature sensor, an electrical impedance sensor, or a mechanical sensor.

16. The method of claim 1, further comprising rewarming or thawing the frozen tissue after a treatment time.

* * * * *